United States Patent
Melzer-Jokisch et al.

(10) Patent No.: US 8,996,156 B2
(45) Date of Patent: Mar. 31, 2015

(54) AUTOMATED REPAIR METHOD AND SYSTEM

(75) Inventors: Torsten Melzer-Jokisch, Neuenhagen bei Berlin (DE); Dimitrios Thomaidis, Berlin (DE); Rolf Wilkenhöner, Kleinmachnow (DE)

(73) Assignee: Siemens Aktiengesellschaft, München (DE)

( * ) Notice: Subject to any disclaimer, the term of this patent is extended or adjusted under 35 U.S.C. 154(b) by 603 days.

(21) Appl. No.: 13/390,765

(22) PCT Filed: Aug. 16, 2010

(86) PCT No.: PCT/EP2010/061893
§ 371 (c)(1),
(2), (4) Date: Feb. 16, 2012

(87) PCT Pub. No.: WO2011/020814
PCT Pub. Date: Feb. 24, 2011

(65) Prior Publication Data
US 2012/0179285 A1     Jul. 12, 2012

(30) Foreign Application Priority Data

Aug. 20, 2009   (EP) .................................... 09010737

(51) Int. Cl.
*G06F 19/00*    (2011.01)
*B23P 6/00*     (2006.01)
*F01D 5/00*     (2006.01)
*G05B 19/4099*  (2006.01)
(Continued)

(52) U.S. Cl.
CPC ................ *B23P 6/007* (2013.01); *F01D 5/005* (2013.01); *G05B 19/4099* (2013.01); *B23K 26/345* (2013.01); *G01N 21/91* (2013.01); *G05B 2219/32228* (2013.01); *F05D 2230/30* (2013.01); *F05D 2230/10* (2013.01)
USPC ............... 700/159; 700/95; 700/96; 700/117; 700/123; 700/162; 700/186

(58) Field of Classification Search
USPC .............. 700/95–96, 117, 123, 159, 162, 186
See application file for complete search history.

(56) References Cited

U.S. PATENT DOCUMENTS 5,956,845 A * 9/1999 Arnold .................. 29/889.1
6,380,512 B1   4/2002 Emer
(Continued)

FOREIGN PATENT DOCUMENTS

DE    8909840 U1    12/1990
EP    0492740 A1    7/1992
(Continued)

*Primary Examiner* — Ronald Hartman, Jr.

(57) ABSTRACT

A method and system for automated repair of a machine component is provided. According to the proposed method, a first geometry of the component, including a damaged portion of the component, is digitalized. A trough is then machined over the damaged portion of the component. The machining is numerically controlled using digitalized geometrical data of the first geometry of the component. A second geometry of the component is then digitalized subsequent to the machining, the second geometry including the trough. Subsequently, a material is deposited over the trough. The deposition of the material is numerically controlled digitalized geometrical data of the second geometry of the component.

14 Claims, 4 Drawing Sheets

(51) Int. Cl.
*B23K 26/34* (2014.01)
*G01N 21/91* (2006.01)

(56) References Cited

U.S. PATENT DOCUMENTS

| | | | |
|---|---|---|---|
| 6,568,077 | B1 | 5/2003 | Hellemann et al. |
| 6,606,541 | B2 * | 8/2003 | Vaidyanathan ............... 700/275 |
| 6,919,956 | B2 | 7/2005 | Kitagawa et al. |
| 7,797,828 | B2 * | 9/2010 | Beeson et al. ........... 29/888.021 |
| 8,096,030 | B2 | 1/2012 | Graichen |
| 8,158,903 | B2 * | 4/2012 | Meier ..................... 219/121.63 |
| 2003/0088980 | A1 * | 5/2003 | Arnold ........................ 29/889.1 |
| 2007/0251072 | A1 * | 11/2007 | Beeson et al. ............. 29/402.01 |
| 2011/0087352 | A1 * | 4/2011 | Krause ........................... 700/98 |

FOREIGN PATENT DOCUMENTS

| | | |
|---|---|---|
| EP | 1153699 A2 | 11/2001 |
| EP | 1312438 A1 | 5/2003 |
| RU | 2235147 C1 | 8/2004 |
| SU | 1655749 A1 | 6/1991 |
| WO | WO 2009050229 A1 | 4/2009 |
| WO | WO 2009105221 A2 | 8/2009 |

* cited by examiner

AUTOMATED REPAIR METHOD AND SYSTEM

CROSS REFERENCE TO RELATED APPLICATIONS

This application is the US National Stage of International Application No. PCT/EP2010/061893, filed Aug. 16, 2010 and claims the benefit thereof. The International Application claims the benefits of European Patent Office application No. 09010737 EP filed Aug. 20, 2009. All of the applications are incorporated by reference herein in their entirety.

FIELD OF INVENTION

The present invention relates to automated repair of machine components. The present invention relates particularly, though not exclusively to automated repairing of a turbomachine component, such as a blade or a vane.

BACKGROUND OF INVENTION

Metallic machine components may be subject to deterioration resulting from use. Turbomachine components, for instance, deteriorate due to mechanical forces, as well as wear due to friction, erosion and corrosion from use in the fluid medium. In particular, turbomachine blades and vanes experience erosion wear on their leading and trailing edges during operation. This progressive deterioration of the blades and vanes reduces the efficiency of the turbomachine. Eventually, the thickness, or other dimensions such as chord width, of the vane or blade are reduced below the minimum allowable serviceable limits, resulting in mandatory disposal or repair of the worn out blade or vane.

In the past, it has often been necessary to completely replace the entirety of the worn turbine blades or vanes. However, for cost reasons, a method of repairing only the worn out portion of the blade or vane instead of completely replacing the entire worn out blade or vane is desirable. Heretofore, worn out blades or vanes have been repaired by machining down the worn out portion, such as the tip, to remove the worn out portion, and then re-applying the missing material, for example, by means of microplasma deposit welding. This process involves manual trenching, welding and re-contouring. Again, such a process is time taking, involves high costs, is manpower intensive and may not be accurate.

SUMMARY OF INVENTION

The object of the present invention is to provide a system and method for repair of a machine component that provides high accuracy and less man-power intensive as compared to the existing process described above.

The above object is achieved by the method according to the claims and the system according to the claims.

The underlying idea of the present invention is to automate the repair process by digitizing the geometry of the component after every operation and using the digitized geometry as an input condition for numerically controlling the subsequent operation. This involves setting up of a data flow of the digitized geometries of the component which is updated after each individual operation of the proposed repair process.

In one embodiment, numerically controlling said machining includes generating a machining path in response to identifying a position of said damaged portion on the said first geometry of the component, based on a received user input. This allows the user or worker to define the areas on the component where damages have occurred on the basis of the delivery guidelines.

In one embodiment, numerically controlling said deposition includes determining a material deposition path in response to identifying a position of the trough on said component, based on a comparison of the digitalized geometrical data of said first geometry to stored reference geometry data of said component. This provides an automated generation of a trajectory for the material deposition.

In an exemplary embodiment, said deposition comprises a process of laser powder cladding. This allows good dimensional control of the welding seam and provides an accurately controllable energy input which permits low heat input and produces small heat affected zones.

In a preferred further embodiment, to remove material overlap after the deposition process and achieve accurate dimensions, said method further comprises:
digitalizing a third geometry of said component after said deposition,
measuring an excess of the deposited material on said component using digitalized geometrical data of said third geometry of the component, and
further machining of said component to remove said measured excess of the deposited material, said further machining being numerically controlled using the digitalized geometrical data of said third geometry.

In a further embodiment, the proposed method comprises a process of coating said component subsequent to said further machining. The protective coating acts as a thermal barrier to protect the component from high temperatures. Such a coating is particularly useful for gas turbine components.

In a further embodiment, said component comprises at least one opening provided by design, wherein said method further comprises:
identifying a position of the design opening on said component, based on a comparison of the digitalized geometrical data of the second geometry of said component to stored reference geometry data of the component,
forming an opening on said component after said process of coating, at said identified position of said design opening.

The position of openings on the component is thus accurately captured in the geometry of the component before the welding process.

In order to enhance measurement accuracy, said reference geometry data includes a digitalized geometrical data of said component after newly manufacturing said component, or digitalized geometrical data of said component after a previous repair of said component, or a digitalized three-dimensional design drawing of said component, or combinations thereof.

For the same reason, in a further embodiment, the proposed method further comprises storing digitalized geometrical data of the component subsequent to a completion of a current repair of the component and using said stored digitalized geometrical data as reference geometry of the component for a subsequent repair of the component.

In order to automate repair, the proposed method comprises storing an updated digitalized geometrical data of said of a geometry of said component after a completed operation of the repair method and using said updated digitalized geometrical data for numerically controlling a subsequent operation of the repair method.

In an exemplary embodiment, said component is a blade or a vane of a turbomachine.

BRIEF DESCRIPTION OF THE DRAWINGS

The present invention is further described hereinafter with reference to illustrated embodiments shown in the accompanying drawings, in which.

DETAILED DESCRIPTION OF INVENTION

The present invention thus provides an automated process for weld repairing a damaged portion of a machine component. The present invention may be used particularly, though not exclusively, for automated repair of a blade or vane of a turbomachine. Hence it should be appreciated that although the embodiments illustrated hereinafter refer particularly to a hollow air cooled blade used in the turbine section of a gas turbine engine, the present invention is equally applicable for repair of other components, such as stationary vanes, or indeed repair of any other metallic machine component.

Figure 1:
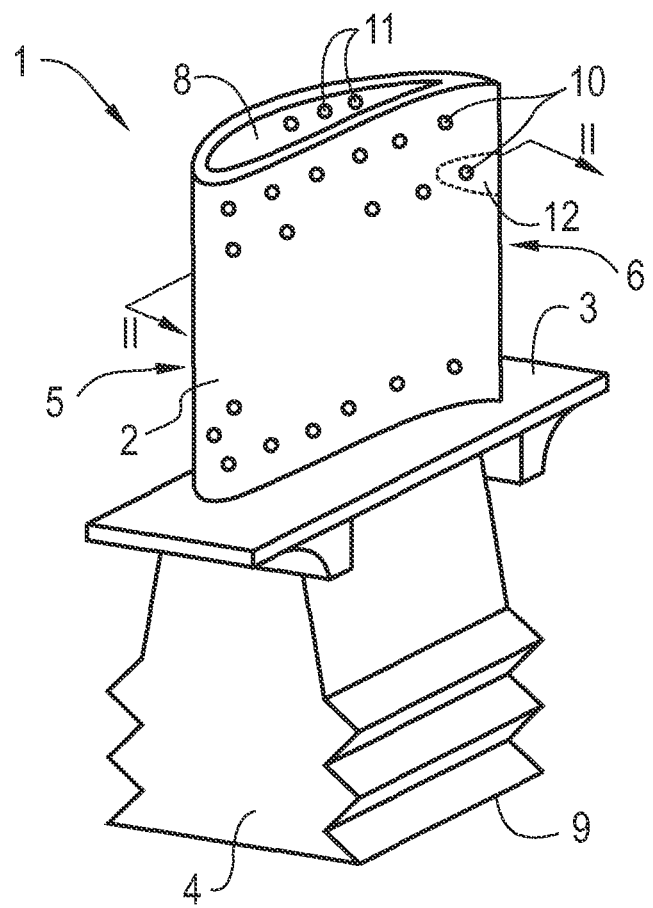
FIG. 1 is a perspective view of a damaged turbine blade that can be repaired using the present invention.
Figure 2A:
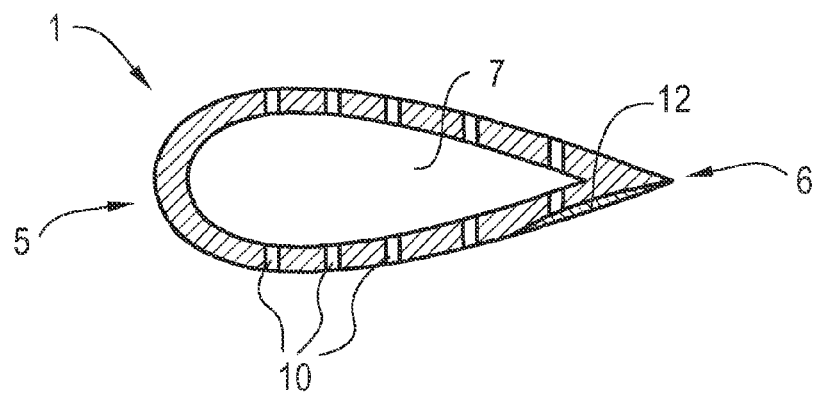
FIG. 2A is a cross-sectional view of the damaged blade.

Referring to FIG. 1 is illustrated a structure of a turbine blade 1, which is to be repaired according to an example embodiment of the present invention. The structure of the blade 1 may be better illustrated also referring to FIG. 2A, which is a cross-sectional view of a section II-II of the blade 1.

The blade 1 has an airfoil portion 2, a platform portion 3 and a root portion 4 for securing the turbine blade 1 to the rotor of a turbine engine. The blade 1 has a leading edge 5 and a trailing edge 6. In the illustrated embodiment, the blade 1 is hollow, having a cavity 7 (visible in the cross-sectional view of the blade shown in FIG. 2A) that extends from the tip 8 of the blade 1 to the base 9 of the root portion 4. The illustrated blade 1 is air-cooled and is designed to have openings, referred to as cooling holes, that extend from the cavity 7 to the external surface of the blade 1. During engine operation, air flows into the cavity 7 and exits the blade 1 though the cooling holes. In the illustrated embodiment, several such cooling holes 10 extend from the cavity 7 to the surface of the airfoil portion. Additionally, several cooling holes 11 may extend from the cavity 7 to the blade tip 8. Although not shown herein, cooling holes may also be provided that extend from the cavity 7 to the trailing edge 6.

In operation, the blade 1 is subject to wear due to mechanical forces, as well as friction, erosion and corrosion from use in the fluid medium. Such wear may damage, for example, a portion 12 of the blade 1. The damaged or worn out portion 12 may include a crack and/or reduced dimensions (such as reduced blade thickness) due to wear, which renders the blade 1 unsuitable for further operation, and hence necessitates a repair of the blade 1.

Figure 3:
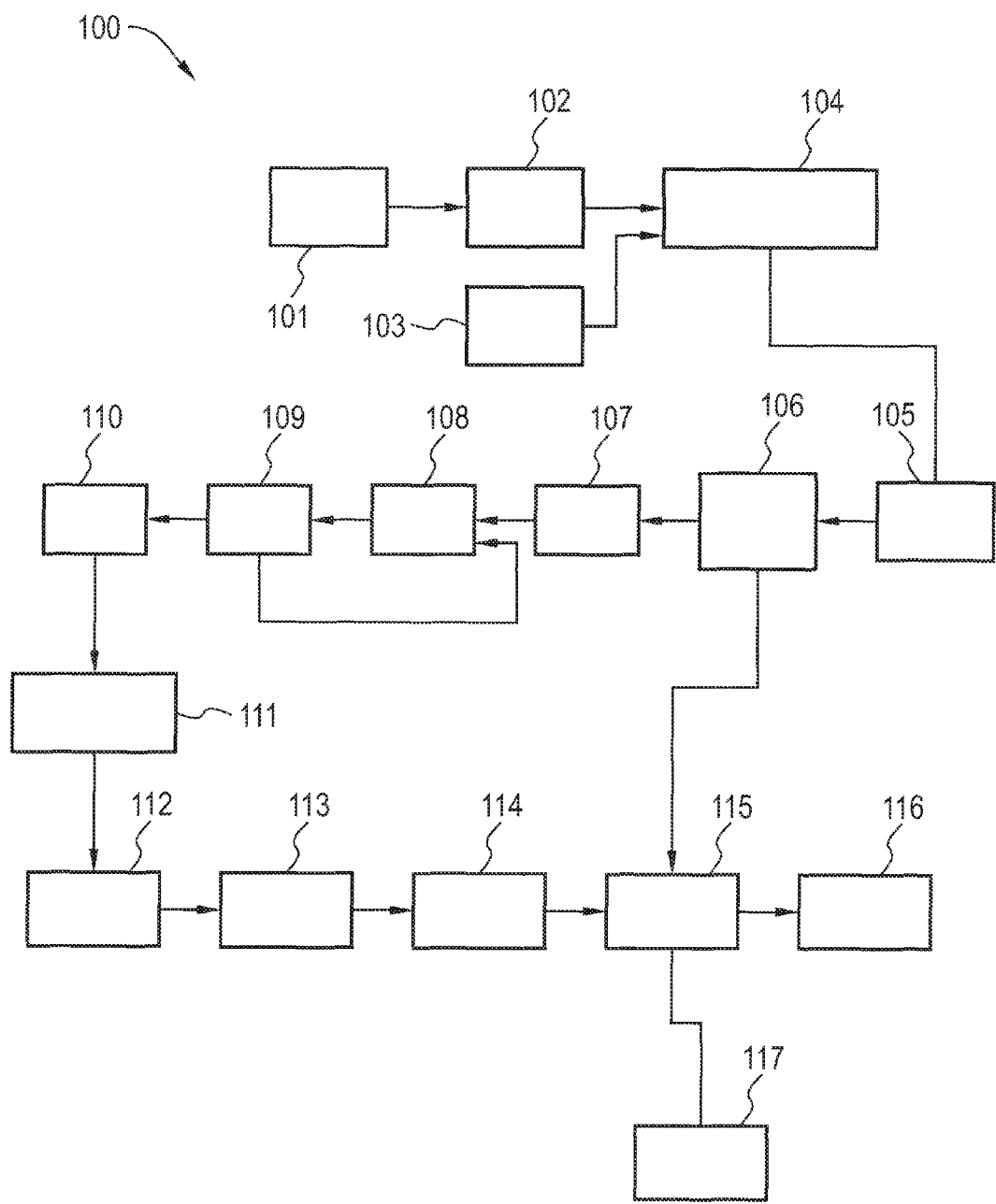
FIG. 3 is a flowchart illustrating a an automated repair process according to one embodiment of the present invention.

Referring to FIG. 3 is illustrated a repair method 100 in accordance with one embodiment of the present invention.

The method 100 is illustrated taking the example of the turbine blade described above. However, such an illustration is merely exemplary and is not meant to be taken in the limiting sense. As illustrated herein, the damaged portion is located on the trailing edge of the airfoil portion. However, the damaged portion may be located in any part of the airfoil portion, platform portion or root portion of the blade, wherein the proposed method is equally applicable.

The repair method 100 begins at block 101 which involves stripping the blade to remove any coating from the blade, to allow a visual inspection of the blade to identify any damaged portion and to ensure that the blade is indeed a candidate for repair. Removing the coating also exposes the base metal of the blade for subsequent machining and welding.

Block 102 involves digitalizing the geometry of the stripped blade including the damaged portion of the blade. This geometry is referred to herein as the first geometry of the blade. As used herein, "digitalizing" of a geometry of a component refers to a process by which the actual geometry of the component is numerically detected and analyzed from an image of the component, wherein the resulting digitalized geometry may be used for the numerical control of the subsequent operation. At block 103, an input is received from a user (worker) to identify the position or location of the damaged portion on the first geometry of the blade. Thus a worker is able to define, on the basis of the delivery guidelines, the areas of the blade where damages have occurred, which need to be repaired.

Figure 2B:
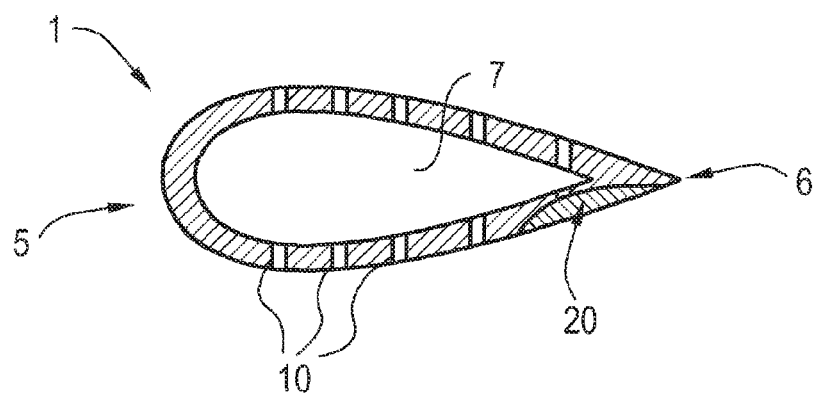
FIG. 2B is a cross-sectional view of the blade after machining.

Block 104 involves the removing of material from the identified damaged portion of the blade by machining, for example, means of milling or any other manufacturing process. In the illustrated embodiment, this machining comprises a milling operation, that is numerically controlled using a first numeric control (NC) program. The first NC program receives as input the digitalized geometrical data of the first geometry of the blade obtained at block 102 and the position of the damaged portion identified at block 102, and generates a machining path (also referred to as tool path) in response thereto. Based on the machining path generated by the first NC program, a trough is milled over the damaged portion of the blade. FIG. 2B is a cross-sectional view of the section II-II of the blade of the illustrated embodiment after the milling operation, showing the trough 20.

Referring back to FIG. 3, at block 105, a test is performed to detect any defects on the blade following the milling operation. Such a test may include, for example, a fluorescent penetrant inspection (FPI) process. Next, at block 106, in order to capture the geometry of the blade subsequent to the milling operation, a second geometry of the blade is digitalized after to the milling operation. The next block 107 involves identifying the position of the trough on the blade. This is done by a reference measurement, involving, for example, a comparison of the digitalized geometrical data of the blade obtained at block 106 to stored reference geometry data of the blade. The stored reference geometry data of the blade may include, for example, digitalized geometrical data of the geometry of the blade when it was newly manufactured, digitalized geometrical data of the geometry of the blade subsequent to a previous repair of the blade, or a digitalized three-dimensional design drawing of the component. Advantageously, for improved measurement accuracy, the reference geometry data used herein may comprise a combination of the above mentioned geometrical data.

Block 108 involves deposition of a filler material to fill up the trough. The filler material may be pre-defined based on the actual material of the blade. Although the deposition process may involve any welding process, a preferred embodiment of the present invention involves laser power build-up welding, also referred to as laser power cladding or microcladding. Laser powder cladding provides good dimensional control of the welding seam and provides an accurately controllable energy input which permits low heat input and produces small heat affected zones. The deposition of the weld material (filler material) is numerically controlled using a second NC program. The second NC program receives as input the digitalized geometrical data of the second geometry of the blade obtained at block 106 and the position of the trough identified at block 107, and generates a material deposition path in response thereto.

Figure 2C:
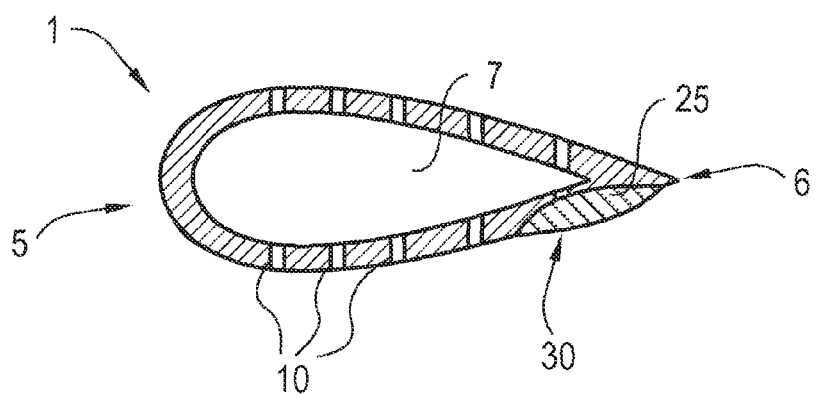
FIG. 2C is a cross-sectional view of the blade after welding.

FIG. 2C shows the cross-sectional view of the blade of the current example subsequent to the weld/deposition process. As shown, the filler material 25 is deposited on to the trough 20 milled on to the blade 1. Also shown herein is a protrusion 30, also referred to as overlap, that generally results from an excess of material deposition during the weld process.

Referring back to FIG. 3, at block 109, a third geometry of the blade is digitalized subsequent to the welding process with the aim of capturing the protrusion or excess material deposit. In some cases, the digitalized geometry of the blade obtained at block 109 may be also used to determine an incomplete welding process, wherein, the blade is subsequently subject to further welding.

The next block 110 involves measuring the excess of material deposit on the blade that needs to be subsequently removed by machining. This excess may be calculated, for example, based on a comparison of the digitalized geometrical data of the third geometry of the blade with stored reference geometry data of the blade that includes allowable tolerances. Subsequently, at block 111, a further machining, including for example, a milling operation, is performed on blade to remove the excess material deposition and re-contour the blade. The re-contouring is numerically controlled using a third NC program, which is generated in response to the digitalized third geometry of the blade obtained at block 109 and the calculation of the excess material to be removed, at block 110.

Subsequent to the re-contouring, a further FPI test may be carried out at block 112 to detect any defects on the blade, following which the blade is re-coated with a protective coating at block 113. The protective coating acts as a thermal barrier to protect the component from high operational temperatures. The next step after re-coating is to re-open the cooling holes or any other openings that are provided on the blade by design. Such openings are best captured in the geometry of blade prior to the welding process. Accordingly, at block 114, a reference measurement is performed, for example, by comparing the digitalized geometrical data of the second geometry of the blade obtained at block 106 to stored reference geometry data, to identify the positions at which the cooling holes (or any other such design opening) need to be re-opened.

Block 115 involves re-opening of the cooling holes on the re-coated blade. The cooling holes are formed at the positions identified at block 114, for example, by a process of laser drilling. This completes the repair process and the repaired blade is sent for quality control and subsequent re-installation (block 116). Advantageously, the geometry of the repaired blade may be further digitalized and stored as reference geometry (block 117) for subsequent repair operation of the blade.

Figure 4:
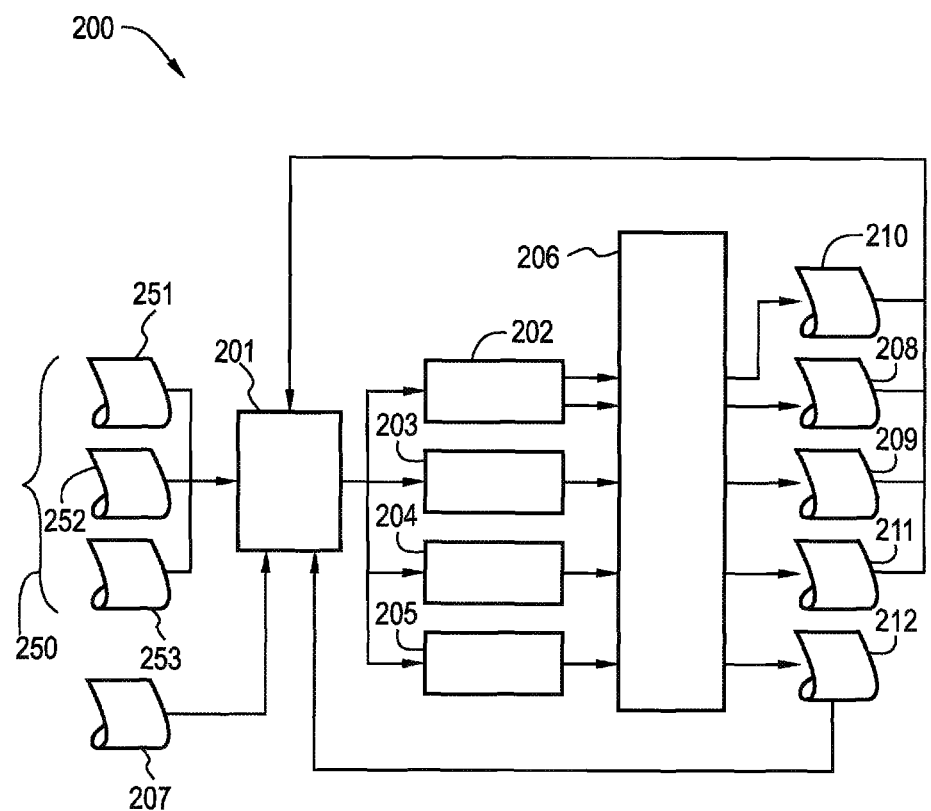
FIG. 4 is a block diagram of illustrating data flow between various elements of an automated repair system according to one embodiment of the present invention.

FIG. 4 shows an automated repair system 200. Data flow between various elements of the system 200 is also illustrated in FIG. 4. The system 200 is configured to carry out the steps of the above-described method. Operations performed by the system 200 are controlled by control means 201. The control means 201 includes, for example, a personal computer, or any other device having processing, storage and input/output circuitry. The control means 201 is adapted to numerically control the operations of the system 200 including machining means 202, welding means 203 and additionally coating means 205 and drilling means 205. The machining means 202 may include, for example, a CNC operated milling machine. The welding means 203 may include, for example a numerically controlled laser powder cladding unit. The drilling means 205 may include, for example, a laser drilling unit.

The illustrated system 200 also includes imaging means 206 for capturing digitalized geometrical data of the geometry of the component (i.e., the blade in this case) subsequent to each operation and feed it to the control means 201. The imaging means 206 may include, for example, a digital camera for capturing an image of the blade, and image processing means for numerically detecting and analyzing the geometry of the blade from the captured image data. The imaging means 206 may alternately include scanning means for three-dimensional scanning the blade based, for example, on laser triangulation or tomographic techniques, and processing means for digitally reconstructing the scanned image data.

The control means 201 is adapted to store the updated digitalized geometrical data of the geometry blade after completed operation and then use it as an input condition for generating a numeric control program for controlling a subsequent operation, while also comparing this updated geometry data to stored reference geometry data 250 of the blade. As reference geometry data, the control means 202 may store, for example, digitalized geometrical data 251 of the blade after manufacture of the blade as well as a digitalized three-dimensional design drawing 252 the blade. If the blade has already been repaired earlier, the geometrical data 253 of the blade geometry after the previous repair may also be stored as reference geometry data 250.

The initial input condition of the process is based on the digitalized geometrical data 207 of the blade including the damaged portion, after stripping the blade to remove any coating. Based on this input, and the position of the damaged portion entered by the user, the control means 201 generates a first NC program for controlling the machining means to machine a trough on the blade over the identified damaged portion.

The geometry of the blade after the machining operation is captured by the imaging means 206 and the digitalized geometrical data 208 of this second geometry of the blade updated into the control means 201. This digitalized geometrical data 208 forms an input condition for generating the NC program for controlling the subsequent operation of welding. Based on a comparison of the digitalized geometrical data 208 to the stored reference geometry data 250, the control means 201 generates a second NC program to control the welding means 201 to deposit a pre-defined material on the trough formed on the blade.

Again, the geometry of the blade after the machining operation is captured by the imaging means 206 and the digitalized geometrical data 209 of this third geometry of the blade updated into the control means 201, which forms an input condition for a subsequent machining operation to remove excess of material deposited during the welding process. Accordingly, based on a comparison of the digitalized geometrical data 208 to the stored reference geometry data 250, the control means 201 generates a third NC program to control the machining means 201 to machine out the excess material from the blade and to re-contour the blade. The re-contoured geometry of the blade is captured by the imaging means 206 and the digitalized data 210 of the re-contoured blade geometry is updated into the control means 210.

Subsequent re-contouring the blade, the blade is coated and the geometry of the coated blade is captured by the imaging means 206. The digitalized data 211 of the geometry of the coated blade is updated into the control means 201, which forms an input condition for the subsequent process of re-opening the cooling holes on the base. Based on the comparison of the digitalized geometrical data 209 of the machined blade and the reference geometry data 250, the control means 201 generates the NC program to control the operation of the drilling means 205 to re-open the cooling holes. Finally, the geometry of the blade after the drilling operation is once again captured by the imaging means 206 and stored into the control means 201, for use as reference geometry data for a subsequent repair process of the component.

Summarizing, the present invention provides a method and system for automated repair of a machine component. According to the proposed method, a first geometry of said component, including a damaged portion of the component, is digitalized. A trough is then machined over said damaged portion of said component. The machining is numerically controlled using digitalized geometrical data of said first geometry of the component. A second geometry of said component is then digitalized subsequent to said machining, said second geometry including said trough. Subsequently, a material is deposited over said trough. The deposition of the material is numerically controlled digitalized geometrical data of said second geometry of said component.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore contemplated that such modifications can be made without departing from the spirit or scope of the present invention as defined by the below-mentioned patent claims.

The invention claimed is:

1. A method for automated repair of a component, comprising:
   digitalizing a first geometry of the component including a damaged portion of the component;
   machining a trough over the damaged portion of the component, the machining being numerically controlled using digitalized geometrical data of the first geometry of the component;
   digitalizing a second geometry of the component subsequent to the machining, the second geometry including the trough;
   depositing a material to fill the trough, the deposition of the material being numerically controlled using digitalized geometrical data of the second geometry of the component;
   digitalizing a third geometry of the component after the deposition;
   measuring an excess of the deposited material on the component using digitalized geometrical data of the third geometry of the component; and
   further machining of the component to remove the measured excess of the deposited material, the further machining being numerically controlled using the digitalized geometrical data of the third geometry,
   wherein numerically controlling the deposition includes determining a material deposition path in response to identifying a position of the trough on the component, based on a comparison of the digitalized geometrical data of the second geometry to stored reference geometry data of the component.

2. The method according to claim 1, wherein numerically controlling the machining includes generating a machining path in response to identifying a position of the damaged portion on the first geometry of the component, based on a received user input.

3. The method according to claim 1, wherein the deposition comprises a process of laser powder cladding.

4. The method according to claim 1, further comprising a process of coating the component subsequent to the further machining.

5. The method according to claim 1,
   wherein the component comprises an opening provided by design, and
   wherein the method further comprises:
      identifying a position of the design opening on the component, based on a comparison of the digitalized geometrical data of the second geometry of the component to stored reference geometry data of the component,
      forming an opening on the component after the process of coating, at the identified position of the design opening.

6. The method according to claim 1, wherein the reference geometry data includes data selected from the group consisting of, a digitalized geometrical data of the component after newly manufacturing the component, digitalized geometrical data of the component after a previous repair of the component, a digitalized three-dimensional design drawing of the component, and combinations thereof.

7. The method according to claim 1, further comprising storing an updated digitalized geometrical data of a geometry of the component after a completed operation of the repair method and using the updated digitalized geometrical data for numerically controlling a subsequent operation of the repair method.

8. The method according to claim 1, further comprising storing digitalized geometrical data of the component subsequent to a completion of a current repair of the component and using the stored digitalized geometrical data as reference geometry of the component for a subsequent repair of the component.

9. The method according to claim 1, wherein the component is a blade or a vane of a turbomachine.

10. A system for automated repair a component, comprising:
   a control means;
   a machining means for machining a trough over a damaged portion of the component using a first numeric control program, wherein the first numeric control program is generated by the control means using digitalized geometrical data of a first geometry of the component that includes the damaged portion; and
   welding means for depositing a material to fill the trough using a second numeric control program,
   wherein the second numeric control program is generated by the control means using digitalized geometrical data of a second geometry of the component after the machining, the second geometry including the trough formed on the component,
   wherein a third geometry including the deposited material is digitized, and
   wherein the digitized third geometry is used as an input for the machining means to machine the component removing an excess of the deposited material.

11. The system according to claim 10, wherein the welding means comprises a computerized numeric control operated laser powder cladding unit.

12. The system according to claim 10, wherein the machining means comprises a computerized numeric control operated milling machine.

13. The system according to claim 10, further comprising imaging means for capturing digitalized geometrical data of the geometries of the component.

14. The system according to claim 13, wherein the control means is adapted to store an updated digitalized geometrical data of a geometry of the component after a completed operation, and to use the updated digitalized geometrical data as an input condition for generating a numeric control program for controlling a subsequent operation.

* * * * *